(12) United States Patent
Mebarak et al.

(10) Patent No.: US 10,898,209 B2
(45) Date of Patent: Jan. 26, 2021

(54) BONE PLATING SYSTEM INCLUDING A DRILL JIG WITH LOCKING ELEMENTS

(71) Applicant: Biomet Manufacturing, LLC, Warsaw, IN (US)

(72) Inventors: Edward Mebarak, Medley, FL (US); Victor Jose Alvarez, Miami, FL (US); Marcus Bourda, Miami, FL (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 15/872,850

(22) Filed: Jan. 16, 2018

(65) Prior Publication Data

US 2018/0199950 A1     Jul. 19, 2018

Related U.S. Application Data

(60) Provisional application No. 62/447,044, filed on Jan. 17, 2017.

(51) Int. Cl.
*A61B 17/17* (2006.01)
*A61B 17/80* (2006.01)
*A61B 17/16* (2006.01)

(52) U.S. Cl.
CPC ...... *A61B 17/1728* (2013.01); *A61B 17/1637* (2013.01); *A61B 17/1615* (2013.01);
(Continued)

(58) Field of Classification Search
CPC .................................................. A61B 17/1728
See application file for complete search history.

(56) References Cited

U.S. PATENT DOCUMENTS

| 2005/0085824 | A1 | 4/2005 | Castaneda |
| 2007/0167953 | A1 | 7/2007 | Prien et al. |

(Continued)

FOREIGN PATENT DOCUMENTS

| CN | 110177512 A | 8/2019 |
| EP | 2072016 | 6/2009 |

(Continued)

OTHER PUBLICATIONS

"International Application Serial No. PCT US2018 013897, International Search Report dated Jun. 19, 2018", 6 pgs.

(Continued)

*Primary Examiner* — Olivia C Chang
(74) *Attorney, Agent, or Firm* — Schwegman Lundberg & Woessner, P.A.

(57) ABSTRACT

Described is a bone plating system and related methods. The system comprises a bone plate and a drill block to be removably attached to the bone plate. The system further comprises a first locking element and a second locking element. The first locking element is configured to be removably attached to the drill block and the bone plate by extending through one drill block hole of the drill block and into one aligned bone screw receiving hole of the bone plate. The second locking element to configured to extend from the drill block and into an opening in the bone plate in order to constrain rotational movement of the bone plate and the drill block with respect to each other when the first locking element is attached to the drill block and the bone plate.

12 Claims, 6 Drawing Sheets

(52) U.S. Cl.
CPC ....... *A61B 17/1622* (2013.01); *A61B 17/1778* (2016.11); *A61B 17/8061* (2013.01)

(56) References Cited

U.S. PATENT DOCUMENTS

| | | | |
|---|---|---|---|
| 2011/0106086 A1* | 5/2011 | Laird | A61B 17/1728 606/70 |
| 2011/0224736 A1* | 9/2011 | Humphrey | A61B 17/1728 606/289 |
| 2014/0243837 A1* | 8/2014 | Mebarak | A61B 17/1728 606/96 |
| 2016/0220286 A1 | 8/2016 | Garvey et al. | |
| 2018/0000496 A1 | 1/2018 | Langdale et al. | |

FOREIGN PATENT DOCUMENTS

| | | |
|---|---|---|
| WO | 2006081483 | 8/2006 |
| WO | 2015138542 | 9/2015 |
| WO | WO-2018136427 A1 | 7/2018 |

OTHER PUBLICATIONS

"International Application Serial No. PCT US2018 013897, Written Opinion dated Jun. 19, 2018", 8 pgs.
"European Application Serial No. 18712722.0, Response to Communication pursuant to Rules 161(2) and 162 EPC filed Apr. 14, 2020", 13 pgs.

* cited by examiner

BONE PLATING SYSTEM INCLUDING A DRILL JIG WITH LOCKING ELEMENTS

CLAIM OF PRIORITY

This application claims the benefit of priority to U.S. Provisional Application Ser. No. 62/447,044, filed on Jan. 17, 2017, which is incorporated herein by reference in its entirety.

FIELD

The present subject matter relates to a bone plating system used in fixation of fractures of bones, such as the humerus, femur, tibia and radius, for example. More specifically, the present subject matter relates to a bone plating system that aids in the location of bone screws and drilling of pilot holes for the placement and fixation of a bone plate to a fractured bone.

BACKGROUND

Fracture to a metaphysis of a long bone can be difficult to treat. Alignment and fixation of a metaphy seal fracture is typically performed by several methods, one of which is plating. Plating utilizes a stabilizing metal plate typically placed against the bone, fixed-angle pegs and screws positioned through the plate and entering drilled holes adjacent an articular bone surface, and bone screws extending from the plate into holes drilled into the bone to provide stabilized fracture fixation.

When fixed-angle pegs and screws are utilized in conjunction with a bone plate, it is necessary to ensure that pilot holes drilled for the fixed-angle pegs and screws are co-axial with axes of holes of the bone plate. Otherwise, the shafts of the fixed-angle pegs and screws will not properly align with the anatomy, and the heads of the fixed-angle pegs and screws will not properly align with the threaded peg/screw holes of the bone plate, potentially resulting in cross-. With the bone plate placed upon a bone, prior to drilling each pilot hole into the bone in alignment with one peg/screw hole in the bone plate, a drill guide can be attached to the bone plate at each peg/screw hole. The drill guide can define a tubular passage which directs a drill bit in a proper orientation for each fixed-angle peg or screw through its particular peg/screw hole. After drilling each pilot hole, the drill guide can be coupled to another subsequent peg/screw hole and the process can be repeated.

OVERVIEW

The present inventors have recognized, among other things, problems associated with the process of attaching a drill guide multiple times during a surgical procedure to implant a bone plate. The process can be laborious. Also, it can be difficult to locate the appropriate angle for threadably coupling the drill guide to a peg/screw hole during the procedure, given that each peg/screw hole may have a discrete axis angle from the other peg/screw holes. Such difficulty can unnecessarily prolong a surgical procedure.

In order to facilitate the drilling of pilot holes, the present inventors propose using an aiming or targeting device, which works like a drilling jig. The aiming or targeting device, also known as a "drill block," can be detachably fixed to the bone plate in a precise position. A benefit of using such a drill block can be the elimination of the need for moving a drill guide around to different peg/screw holes in a bone plate, thereby reducing the duration of the surgical procedure. The inventors have recognized, however, that the drill block needs to be well secured to the bone plate while also being easily and quickly detachable from the bone plate once the bone plate is secured to the bone. Another benefit of the inventive bone plating system is that it includes a drill block that can be easily attached and detached from the bone plate by insertion and removal of a single locking element, otherwise known as a drill block lock. The ability of the drill block to be removed so easily by removing one locking element simplifies the detachment process. A second locking element is included on the drill block to ensure that the drill block cannot be rotated or detached from the bone plate unless the first locking element is removed. However, the second locking element preferably does not require removal, but is rendered ineffective in preventing removal of the drill block from the bone plate or rotation of the drill block with respect to the bone plate if the first locking element is removed.

These and other examples and features of the present apparatuses, systems and methods will be set forth in part in the following Detailed Description. This Overview is intended to provide non-limiting examples of the present subject matter—it is not intended to provide an exclusive or exhaustive explanation. The Detailed Description below is included to provide further information about the present apparatuses and methods.

BRIEF DESCRIPTION OF THE DRAWINGS

In the drawings, which are not necessarily drawn to scale, like numerals can describe similar components in different views. The drawings illustrate generally, by way of example, but not by way of limitation, various examples discussed in the present document.

DETAILED DESCRIPTION

Figure 1:
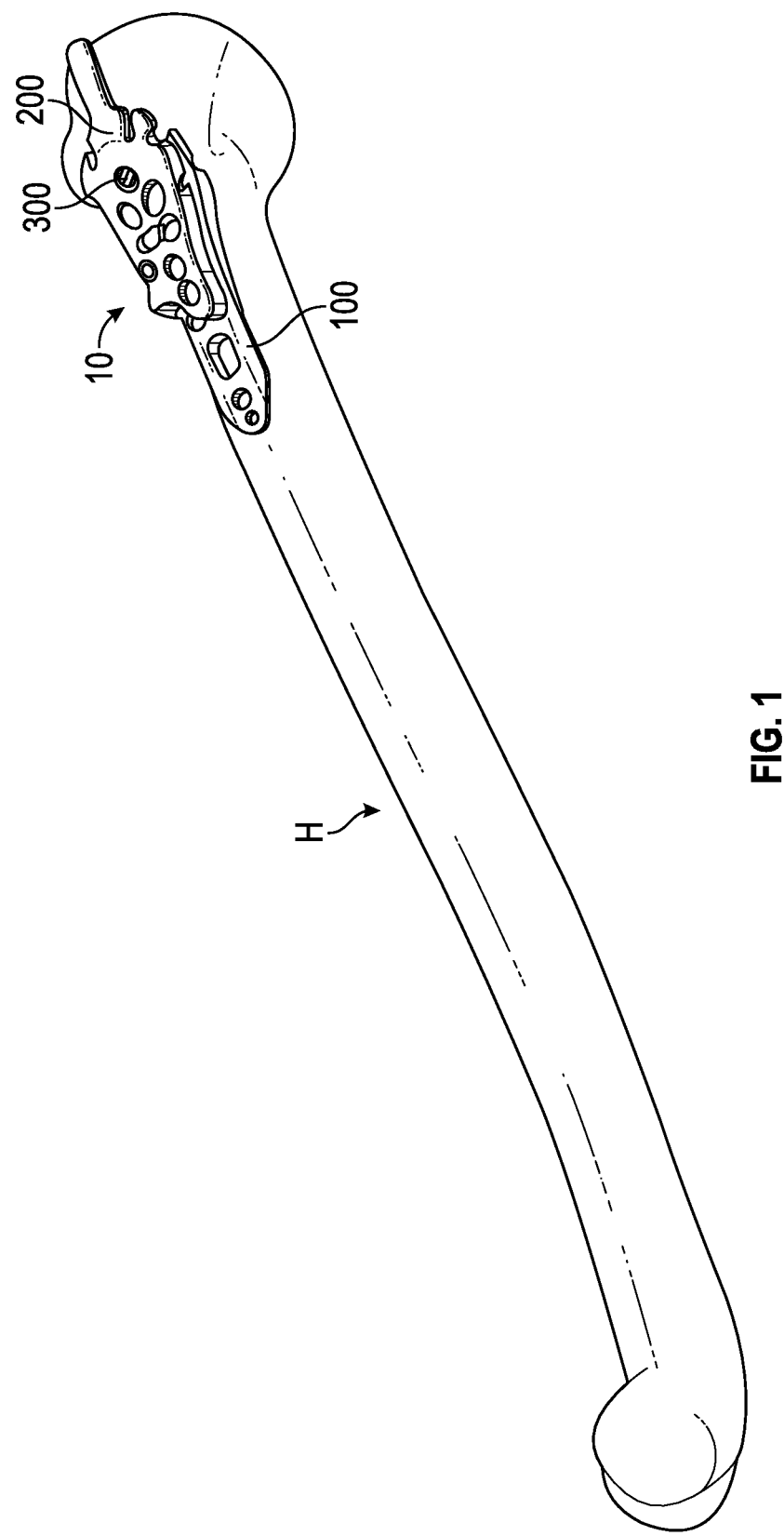
FIG. 1 shows a perspective view of one embodiment of the bone plating system, according to the present disclosure, implanted on a humerus.

With reference to the human body and components of the system described herein which are intended to be implanted in the human body, the terms "proximal" and "distal" are defined in reference to the location at which a limb is connected to the torso, with the term "proximal" being the end of the limb, bone or plate closer to the torso, and the term "distal" being the end of the limb, bone or plate further from the torso. In addition, the term "lower" and "upper" in reference to plate surfaces are designations in which the lower surface is that surface closer to or seating on the bone and the upper surface is that surface opposite the lower surface.

The present application relates to a bone plating system for fixation of bone. The system includes: a bone plate having an upper surface and a lower, bone-contacting surface; a drill block (otherwise known as a "jig") that can be coupled to the bone plate in order to provide a plurality of openings or holes through which bone screws can be threaded in desired orientations to attach the bone plate to bone; and, a first locking element or "drill block lock" (one example of which is a "drill guide") that can extend through one of the openings or holes in the drill block and into an opening or hole in the bone plate in order to hold the bone plate and the drill block together for as long as desired. In addition, both the drill block and the bone plate have a coordinating second locking element that allows the drill block and bone plate, together with the drill block lock, to be held together without the drill block being able to rotate with respect to the bone plate or be detached. The second locking element can be a pin, for example, located on the drill block that can fit into a coordinating opening hole or orifice in the bone plate. The first locking element and the second locking element can be arranged such that longitudinal axes that extend through the first locking element and the second locking element are not parallel to each other. In other words, an angular orientation of the first locking element with respect to the drill block and an angular orientation of the second locking element with respect to the drill block are not the same. Accordingly, the drill block cannot be removed from, or rotated with respect to, the bone plate unless the first locking element is removed.

The bone plate and drill block can be assembled together during manufacture or can be assembled just prior to implantation by a surgeon, for example, by using the first locking element (or drill block lock) and the second locking element to hold the other two components together. The assembly of the bone plate, the drill block and the drill block lock can then be placed in contact with a bone, such as a humerus, by the surgeon, where the bone plate is desired to be attached. A drill can then be inserted through one or more of a plurality of holes or openings in the drill block that coordinate with corresponding holes or opening in the bone plate, and holes can be drilled in the bone. Next, bone screws or pegs can then be inserted in the drilled holes. Once all desired bone screws are screwed or pegs are placed into the bone through the drill block and the bone plate, the drill block lock (or first locking element) can be removed, which can then allow the drill block to be easily removed from the bone plate and from a patient's body. The bone plate can then be left in place in the patient and can remain secured to the bone.

Figure 2:
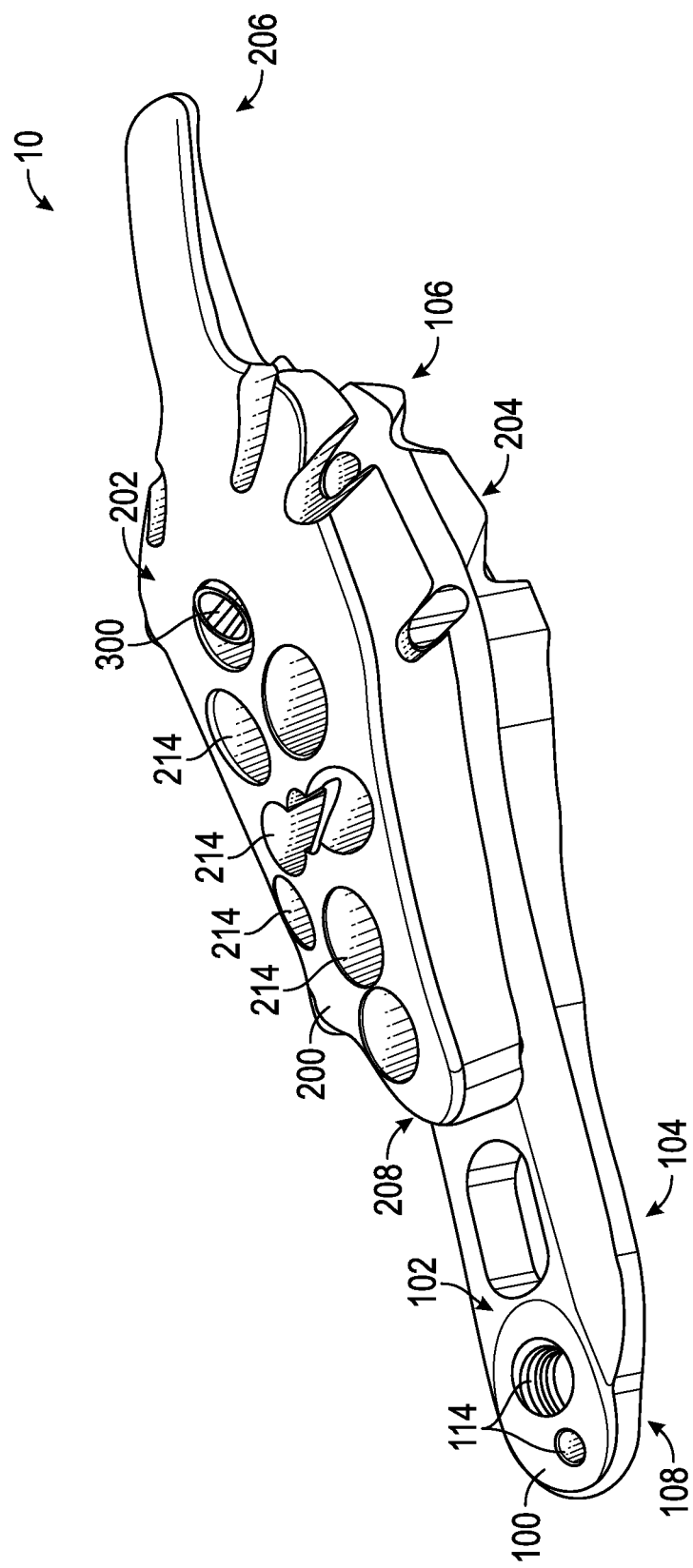
FIG. 2 shows a close-up, perspective view of the bone plating system of FIG. 1.
Figure 3:
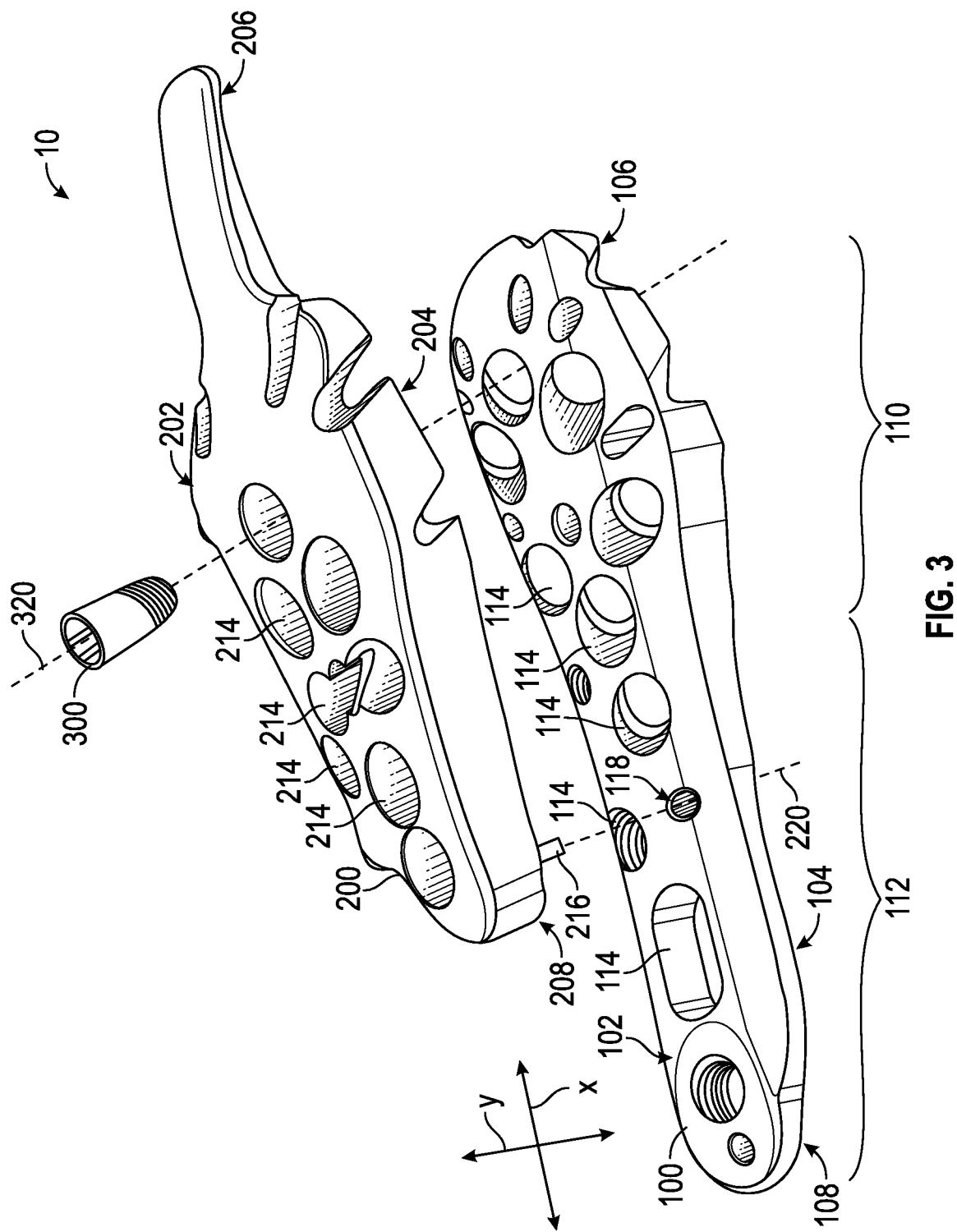
FIG. 3 shows an exploded view of the bone plating system of FIGS. 1-2.

Referring to FIGS. 1-3, the figures illustrate an inventive bone plating system 10 in accordance with an embodiment of the present disclosure. FIG. 1 also shows a humerus bone H, with the embodiment of the inventive bone plating system 10 placed adjacent a proximal end of the humerus bone H. The system 10 can include a bone plate 100, a drill block 200 and a drill block lock 300. The bone plate 100 of the system 10 can be placed in direct contact with the humerus bone H. The drill block 200 can be located on top of the bone plate 100, and the drill block lock 300 can couple or hold the bone plate 100 and drill block 200 together. The figures show an embodiment of bone plating system 10, according to the present disclosure, specifically designed for use on the proximal humerus. In order to secure the bone plating system 10 to the humerus H, in FIG. 1, a plurality of bone screws can be inserted and through the holes shown on an upper surface of drill block 200, then through corresponding holes in bone plate 100, and into drilled holes in the humerus bone H. However, it is contemplated that the inventive bone plating system 10 can be alternatively designed for other bones as well, such as the femur, tibia and radius, for example.

Referring specifically to FIGS. 2-3, the figures illustrate close-up views of the inventive bone plating system 10 of FIG. 1, with FIG. 2 being a perspective, assembled view and FIG. 3 being a close-up, exploded view. As shown, bone plate 100 can have an upper surface 102 and a lower, bone-contacting surface 104. Bone plate 100 can have a proximal end 106 and a distal end 108. The lower, bone-contacting surface 104 of bone plate 100 can include a curved surface to fit the contours of the proximal humerus, for example, and a portion of the shaft of the bone. Bone plate 100 can be shaped and/or sized to fit near the proximal end of the humerus, as shown in FIG. 1. However, other shapes and/or sizes of the bone plate 100 are contemplated to be used on different bones, as well as on different sizes of patients' bones.

As shown in FIG. 3, bone plate 100 can include a head portion 110 configured and dimensioned to conform to at least a portion of the head of the proximal humerus, if the humerus is the bone upon which the bone plate 100 is to be implanted. The head portion 110 can be generally curved and nonlinear in shape. The bone plate 100 can also include a shaft portion 112 that can be generally linear to conform to at least a portion of the shaft of the bone. The shape and size of the head portion 110 and shaft portion 112 can vary depending upon the size and shape of the bone plate 100 used in the bone plating system 10. The bone plate 100 shown is just one example of such a bone plate that can be used on a humerus, but other bone plates for other bones are also contemplated, and can have various shapes, sizes and configurations.

As shown in FIGS. 1-3, the bone plate 100 can include a plurality of bone screw receiving holes, openings, through bores, or apertures, etc., 114 at a plurality of different locations. The plurality of bone screw receiving holes 114 can accommodate a bone screw or peg and can be threaded and/or non-threaded holes. The bone screw receiving holes 114 can extend through the bone plate 100 from the upper surface 102 to the bone-contacting lower surface 104. The plurality of bone screw receiving holes 114 can accommodate bone screws and pegs or can alternatively accommodate other tools or attachment devices, by which the bone plate 100 can be attached to the bone and/or by which the bone plate 100 can be attached to the drill block 200.

The plurality of bone screw receiving holes 114 need not be the same size. Likewise, some or all of the bone screw receiving holes 114 need not have a circular cross-section. Rather, the bone screw receiving holes 114 may be elongated in a horizontal direction or may take on shapes such as triangular or rectangular. Moreover, some or all of the bone screw receiving holes 114 need not have a constant circular cross-section.

As shown, the bone screw receiving holes 114 can be at various angular orientations with respect to each other and the bone plate. In particular, in FIG. 3, the bone screw receiving holes 114 shown in the head portion 110 are angularly divergent. The bone screw receiving holes 114 being divergent can help to stabilize a fracture in a head of a bone to which the bone plate 100 is attached by allowing bone screws that extend through the holes to diverge into different areas of the fractured head of a bone, for example.

Other angular orientations and locations of bone screw receiving holes 114 besides those shown are also contemplated.

Bone plate 100 can be formed of titanium, stainless steel, cobalt chrome, plastic—such as polyetheretherketone (PEEK), polyethylene, ultra high molecular weight polyethylene (UHMWPE), or a carbon composite—resorbable polylactic acid (PLA), polyglycolic acid (PGA), combinations or alloy s of such materials or any other appropriate material that has sufficient strength to be secured to and hold bone, while also having sufficient biocompatibility to be implanted into a body. Although the above list of materials includes many typical materials out of which bone plates are made, it should be understood that bone plates comprised of any appropriate, biocompatible material are within the scope of this disclosure.

As shown in FIGS. 1-3, drill block 200 can be placed on or in contact with an upper surface 102 of bone plate 100. Drill block 200 can have an upper surface 202 and a lower surface 204. At least a portion of the lower surface 204 can contact the bone plate 100. A portion of the lower surface 204 of the drill block 200 can additionally contact the bone itself, as shown in FIG. 1. Drill block 200 can have a proximal end 206 and a distal end 208. Drill block 200 can be shaped and/or sized to fit on at least a portion of a bone plate and can additionally be shaped and/or sized to fit on at least a portion of a proximal end of a humerus, as shown. A portion of the drill block 200 including the proximal end 206 can optionally comprise a proximal extension (as shown in FIG. 1) that can contact a proximal end of the humerus H. Such a proximal extension is optional, but can assist in proper placement of the drill block 200 on the humerus H. The proximal extension, otherwise known as a "nose portion" of the drill block 200, can project tangentially with an articular surface of the humerus H. Other shapes and/or sizes of the drill block 200, other than those shown or described herein, are contemplated to be used on different sizes of patients, different bone plates and different bones.

Drill block 200 can also include a plurality of drill block holes, openings, through bores, or apertures, etc., 214 at a plurality of different locations. The drill block holes 214 can be threaded and/or non-threaded holes. As shown in FIG. 2, the drill block holes 214 coordinate with the bone screw (or peg) receiving holes 114 of the bone plate 100. Like the bone screw receiving holes 114 of the bone plate 100, the drill block holes 214 of the drill block 200 can be at various angular orientations with respect to each other and the drill block 200. The drill block holes 214 can extend through the drill block 200 from the upper surface 202 to the lower surface 204. The plurality of drill block holes 214 can accommodate bone screws and pegs or other tools or attachment devices, by which the drill block 200 can be attached to the bone plate 100, for example.

The plurality of drill block holes 214 need not be the same size. Rather certain of the drill block holes 214 may have a circular cross-section with a diameter larger than the diameter of other circular cross-section holes 214. Likewise, some or all of the drill block holes 214 need not have a circular cross-section. Rather, the drill block holes 214 may be elongated in a horizontal direction or may take on shapes such as a triangular shape or a rectangular shape. Moreover, some or all of the drill block holes 214 need not have a constant circular cross-section, which can be due to the bone plate and/or the bone having an irregular, or not normal, surface. The drill block holes 214 can also be compound angled holes or projected cylinders.

Drill block 200 can be made of similar materials to those of the bone plate 100. For example, drill block 200 can be formed of titanium, stainless steel, aluminum, cobalt chrome, plastic—such as polyetheretherketone (PEEK), polyethylene, ultra high molecular weight polyethylene (UHMWPE), or a carbon composite—resorbable polylactic acid (PLA), polyglycolic acid (PGA), combinations or alloys of such materials or any other appropriate material that has sufficient strength to be secured to the bone plate 100, while also having sufficient biocompatibility to be temporarily in contact with a body. Although the above list of materials includes many typical materials out of which drill blocks can be made, it should be understood that drill blocks comprised of any appropriate material are within the scope of this disclosure.

Drill block lock 300, otherwise known as a first locking element of the system 10, can be placed within one hole of a plurality of drill block holes 214 in the drill block 200. Drill block lock 300 also extends into one bone screw receiving hole 114 (visible in FIG. 3) of a plurality of bone screw receiving holes 114 in the bone plate 100 that coordinates with the drill block hole 214 of drill block 200 into which the drill block lock 300 is inserted. The coordinating holes 114, 214 of the bone plate 100 and the drill block 200, respectively, can be axially aligned such that the drill block lock 300 extends through and along the longitudinal axes of both holes 114, 214. FIG. 3 illustrates how the bone plate 100, drill block 220 and drill block lock 300 can line up along a longitudinal axis 320 of both holes 114, 214 through which the drill block lock 300 extends.

Figure 5:
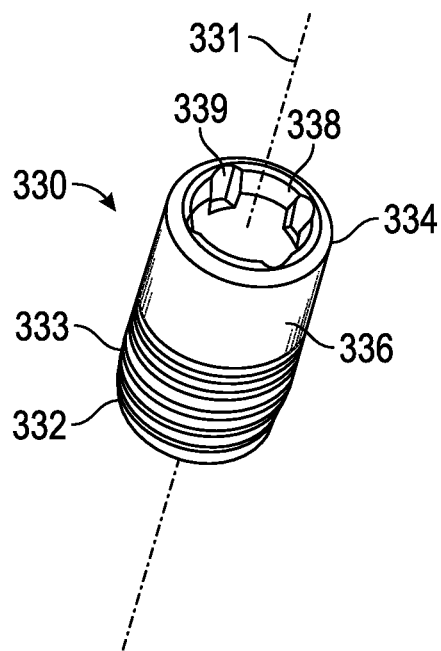
FIG. 5 shows a close-up, perspective view of another embodiment of a bone plating system, according to the present disclosure.
Figure 6:
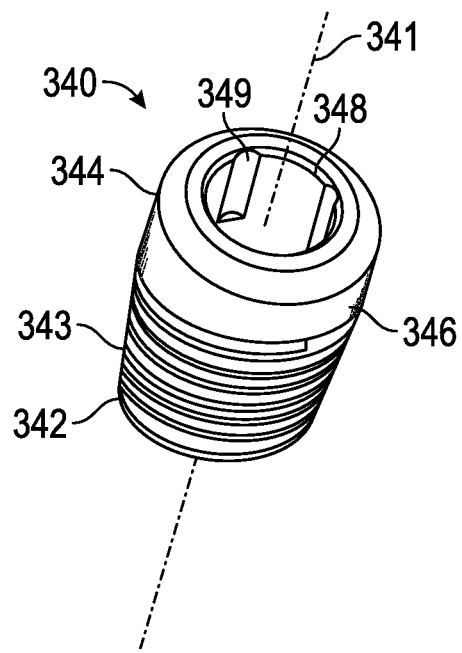
FIG. 6 is a perspective view of one embodiment of a drill block lock that can be part of the bone plating system, according to the present disclosure.

Drill block lock 300 can be a commonly used drill guide as known in the art. FIGS. 5-6 show perspective views of two different, possible embodiments of the drill block lock 330, 340. Other designs or embodiments of the drill block lock are also contemplated, however. The drill block lock can be any peg or component or any other locking element that can fit in one of the drill block holes, such as 214, for example, and into a coordinating bone plate hole, such as 114, for example. The drill block lock can serve to couple the bone plate 100 and the drill block 200 together. The drill block lock 300 can include threading or may be non-threaded. The drill block lock 300 can be solid or can have an opening extending there through. The drill block lock can have any appropriate cross-sectional shape, such as a circular, or a rectangular, cross-sectional shape, that can coordinate with holes in the drill block 200 and the bone plate 100.

FIG. 5 is a perspective view of a first exemplary drill block lock, or first locking element, 330 for use in the inventive system 10. Drill block lock 330 can include a cylindrically-shaped body 336 having a distal end 332, a proximal end 334 and a longitudinal bore 338. The longitudinal bore 338 can have a longitudinal axis 331 and can be shaped and sized for guiding a conventional bone drill. Distal end 332 can include threads 333 for removable attachment to, or threadable engagement with, a threaded aperture of the drill block 200 as well as the bone plate 100, such that longitudinal axis 331 can be collinear with an axis of the threaded aperture in the drill block 200, for example. Proximal end 334 can include four indentations 339 spaced evenly apart on the periphery of bore 338 for receiving a square drive tip, for example, of a drill. However, other numbers of indentations and other shapes of drills are contemplated by the disclosure.

FIG. 6 is a perspective view of a second exemplary drill block lock 340 for use in the inventive system 10. Second drill block lock 340 can include a cylindrically-shaped body 346 having a distal end 342, a proximal end 344, and a longitudinal bore 348 having a longitudinal axis 341. Similar to drill block lock 330, distal end 342 can include threads 343 for removable attachment to a threaded aperture of the drill block 200 as well as the bone plate 100, such that longitudinal axis 341 can be collinear with an axis of the threaded aperture. Proximal end 344 can include four indentations 349 spaced evenly apart on the periphery of bore 348 for receiving a square drive tip, for example, of a drill.

Materials utilized in the manufacture of the drill block lock 300 (and 330, 340) can be those typically used in surgical equipment. Stainless steel, titanium, and other robust metals that may be sterilized can be used. Aluminum, anodized aluminum, and rigid polymers also can be utilized. Carbon fiber-reinforced polymers can be utilized, as they are lightweight, extremely strong and may be sterilized. Drill block locks utilizing a combination of materials can also be used.

Figure 4:
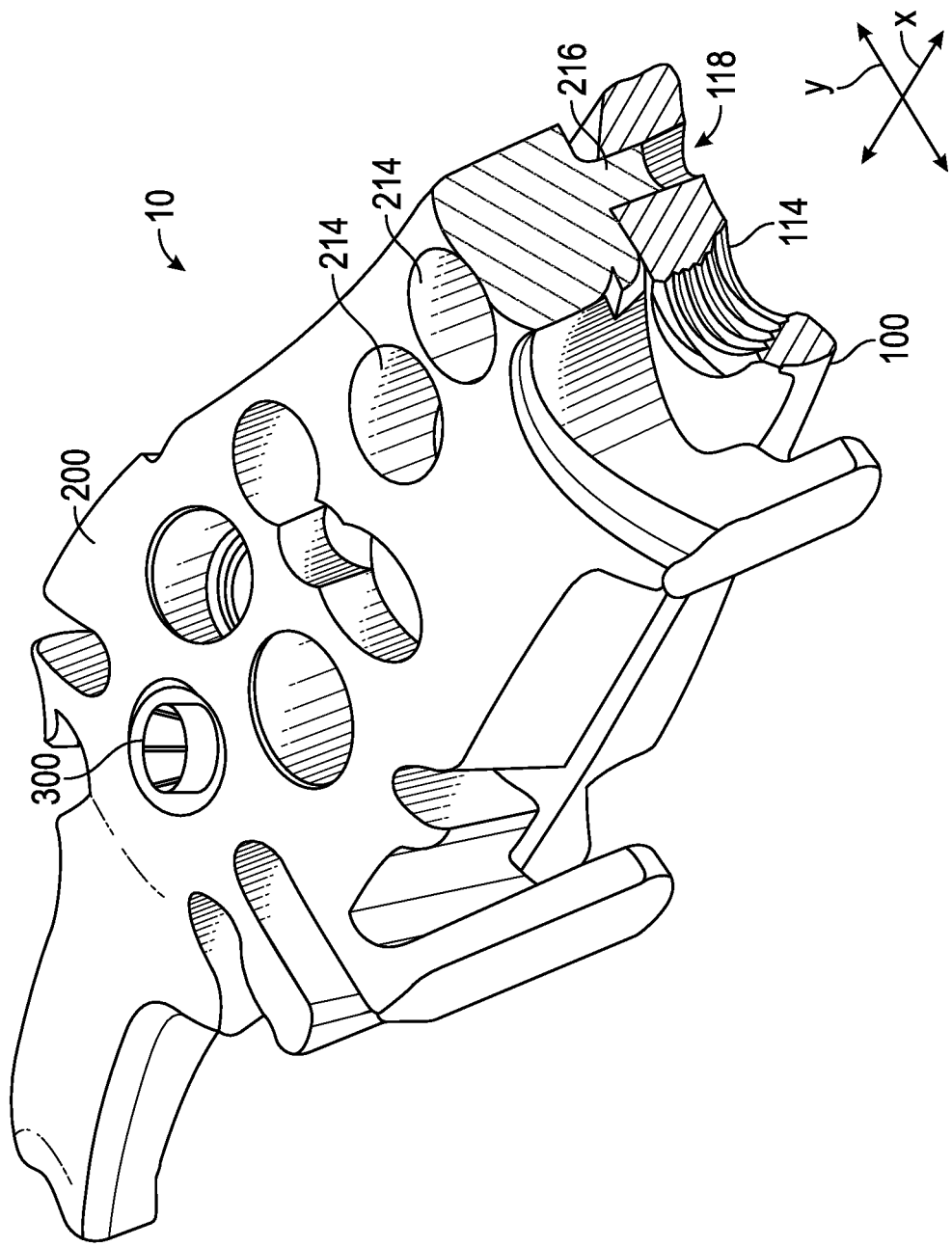
FIG. 4 is a cut-away perspective view of the bone plating system of FIGS. 1-3.

In addition to drill block lock 300, or first locking element, a second locking element is used to hold the drill block 200 and the bone plate 100 together. One exemplary second locking element, shown in FIGS. 3-4, can be located on, or made part of, the drill block 200. The exemplary second locking element can be mounted on, attached to, or made part of the drill block 200, and can be a pin 216 that extends from the lower surface 204 of drill block 200. The second locking element can be engageable with a bone plate hole 118 in at least the area of the upper surface 102 of bone plate 100. The second locking element, one example of which is pin 216, can constrain movement of the drill block 200 with respect to the bone plate 100 in the x-direction and the y-direction, with x and y axes indicated on both FIGS. 3 and 4. The pin 216 that fits in a corresponding opening in the bone plate 100 can have any shape that can constrain movement in the two directions. The cut-away view of bone plating system 10 in FIG. 4 shows how pin 216 can fit within opening 118 in bone plate 100 in order to constrain the drill block 200 from moving with respect to the bone plate 100, together with the first locking element 300.

Pin 216 is one embodiment of such a second locking element, and other possible second locking elements are also contemplated by the disclosure. For example, at least one other contemplated second locking element can comprise any portion of the lower surface 204 of the drill block 200 (or a feature coupled to the drill block 200 or made part of the drill block 200) that can contact a portion of the bone plate 100 (or enter an opening in the bone plate), such that when the bone plate 100 is in contact with the second locking element, the combination of corresponding features of the two components constrains freedom of rotation of the bone plate 100 and the drill block 200 with respect to each other in at least two directions. The two directions are indicated by the x and y axes in FIGS. 3-4.

Figure 7:
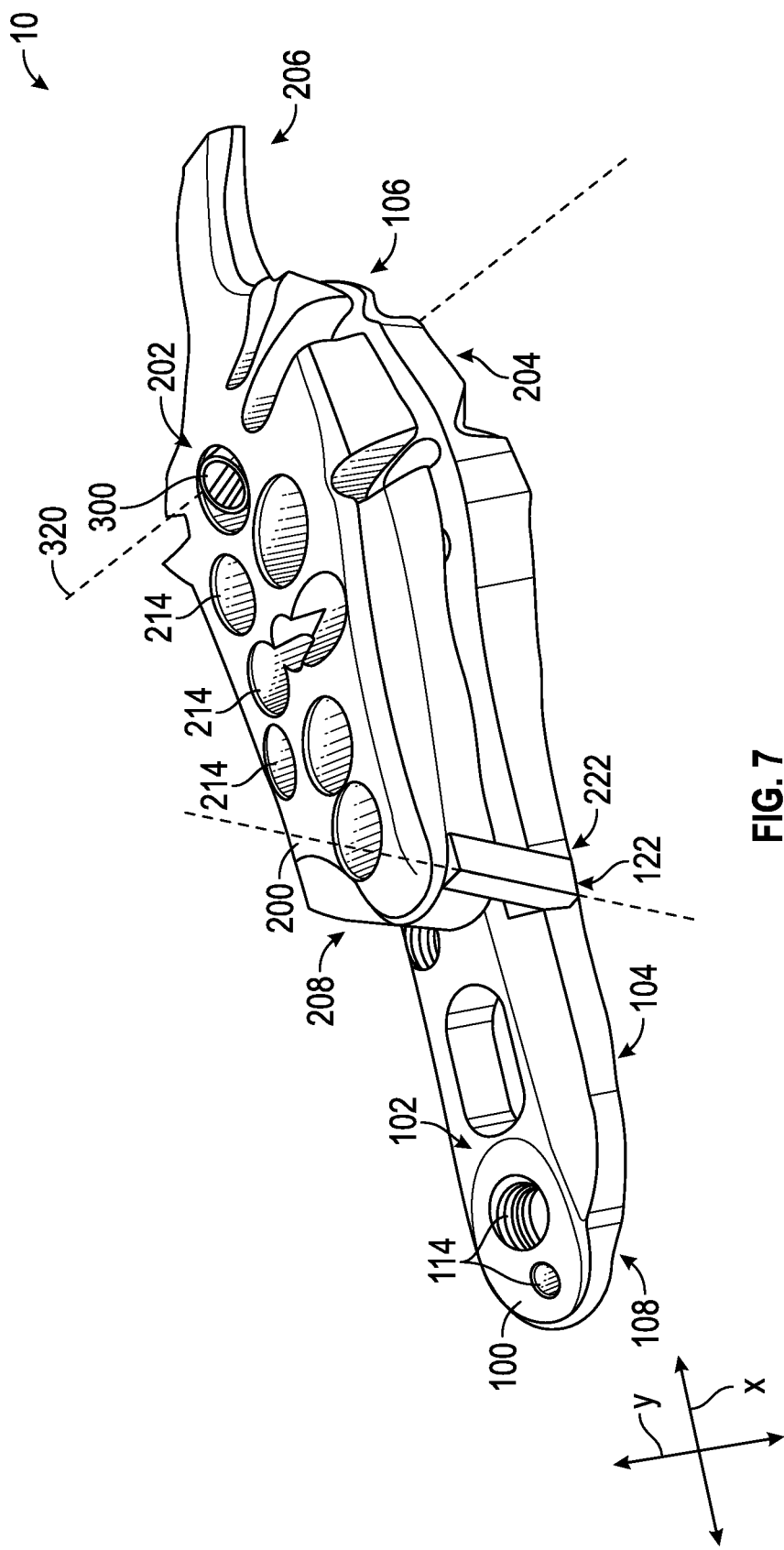
FIG. 7 is a perspective view of a second embodiment of a drill block lock that can be part of the bone plating system, according to the present disclosure.

FIG. 7 illustrates another embodiment of a second locking element 222 that can be attached to, extend from, or be made to form part of the drill block 200. Second locking element 222 can have a rectangular-shaped or square-shaped cross-section, which can fit in a correspondingly-shaped opening cut-out or indentation 122 in bone plate 100. The corresponding rectangular or square shapes, for example, of the second locking element 222 and the indentation 122 allow at least two flat portions or sides of the rectangles or squares to contact each other and constrain movement of the drill block 200 and the bone plate 100 with respect to each other in the x and y axes.

The second locking element, such as 216 or 222, can be included on the drill block 200 to ensure that the drill block 200 cannot be rotated or detached from the bone plate 100 unless the first locking element 300 is removed. However, the second locking element, such as 216 or 222, preferably does not require removal, but is rendered ineffective at preventing removal of the drill block 200 from the bone plate 100 and rotation of the drill block 200 with respect to the bone plate 100 when the first locking element 300 is removed.

The longitudinal axis of the drill block lock 300 (axis 320 in FIG. 3) and a longitudinal axis extending through either the pin 216 (axis 220 in FIG. 3) or the second locking element 222 (axis 224 in FIG. 5) cannot be parallel to each other, otherwise the drill block 200 could be detached from the bone plate 100 even with the drill block lock 300 in place. As long as the two axes (220 and 320, or 224 and 320) are not parallel, then the drill block lock 300 will hold the drill block 200 and bone plate 100 together. In other words, an angular orientation of drill block lock 300 in the drill block hole 214 into which it is inserted with respect to the drill block 200 cannot be the same as (i.e., is different than) an angular orientation of either the pin 216 with respect to the drill block 200 or the second locking element 222 with respect to the drill block 200, otherwise, the drill block 200 could be removed from the bone plate 100 without the drill block lock 300 being removed.

FIG. 3 shows axis 320 that extends through the drill block lock 300 and through the coordinating holes 214, 114 in the drill block 200 and bone plate 100, respectively. The figure also shows axis 220 that extends through pin 216 on drill block 200 and through opening 118 in bone plate 100. The two axes 320, 220 are not parallel, therefore the drill block 200 cannot be removed from the bone plate 100 unless the drill block lock 300 is removed. FIG. 7 shows axis 320 that extends through the drill block lock 300 and through the coordinating holes 214, 114 in the drill block 200 and bone plate 100, respectively. The figure also shows axis 224 that extends through the second locking element 222 of drill block 200 and through the indentation 122 in bone plate 100. The two axes 320 and 224 are not parallel, therefore the drill block 200 cannot be removed from the bone plate 100 unless the drill block lock 300 is removed.

With the present inventive bone plating system 10, the bone plate 100 can be provided to the surgeon preassembled with the drill guide 200. The preassembled bone plating system is beneficial because then it is not necessary for the surgeon or assistant to attach the components during a procedure. In this way, the surgeon may quickly drill several bone holes and insert bone screws. The drill block 200 can also be quickly removed by removing only the drill block lock 300 once bone screws are in place, thereby allowing the procedure to take less time than without the use of the inventive bone plating system.

The present disclosure includes a method of fixating a fracture of a bone. One step of the method can be providing a bone plate including a plurality of bone screw receiving holes. Another step can be providing a drill block to be removably attached to the bone plate and including a plurality of drill block holes and a first locking element extending from the drill block. A further step can be applying the drill block to the bone plate such that the first locking element is inserted in an opening in the bone plate. Yet another step can be attaching the bone plate to the drill block by inserting a second locking element through one of the plurality of drill block holes and into one of the plurality of bone screw receiving holes that is aligned with the one of the plurality of drill block holes in order to constrain rotational movement of the bone plate and the drill block with respect to each other when the second locking element is attached to the drill block and the bone plate. A next step can be applying the bone plate to the bone adjacent the fracture. Yet another step can be inserting a drill through one of the plurality of drill block holes and an aligned bone screw receiving hole of the bone plate and drilling a hole in the bone using the drill, and repeating this step until a desired number of holes are drilled in the bone. Finally, another step can be securing the bone plate to the bone by inserting a plurality of bone screws through the plurality drill block holes and the plurality of bone screw receiving holes, and into the holes drilled in the bone. The method can further include the steps of: removing the second locking element; and removing the drill block from the bone plate.

ADDITIONAL NOTES AND EXAMPLES

To further illustrate the bone plating system and methods disclosed herein, the following non-limiting examples are provided:

Example 1 includes a bone plating system comprising a bone plate; a drill block removably attachable to the bone plate; a first locking element configured to be removably attached to the drill block and the bone plate by extending through a drill block hole of the drill block and into an aligned bone screw receiving hole of the bone plate; and a second locking element configured to extend from the drill block and into an opening in the bone plate in order to constrain rotational movement of the bone plate and the drill block with respect to each other when the first locking element is attached to the drill block and the bone plate.

Example 2 includes the bone plating system of example 1, wherein an angular orientation of the first locking element with respect to the drill block and an angular orientation of the second locking element with respect to the drill block are different.

Example 3 includes the bone plating system of example 1, wherein an angular orientation of the first locking element with respect to the drill block and an angular orientation of the second locking element with respect to the drill block are not parallel.

Example 4 includes the bone plating system of any one of examples 1-3, wherein the second locking element comprises a pin.

Example 5 includes the bone plating system of any one of examples 1-4, wherein the first locking element comprises a drill guide.

Example 6 includes a bone plating system comprising a drill block having a first surface for contacting a first surface of a bone plate and a second surface opposite the first surface, and at least one drill block hole extending from the first surface to the second surface of the drill block; the bone plate having the first surface for contacting the drill block, a second surface for contacting a bone, and at least two bone screw receiving holes extending from the first surface to the second surface of the bone plate, wherein one of the at least two bone screw receiving holes is alignable with the at least one drill block hole; a first locking element configured to be removably attached to the drill block and the bone plate by extending through the at least one drill block hole of the drill block and into the one of the at least two bone screw receiving holes of the bone plate that is alignable with the at least one drill block hole; and a second locking element extending from the first surface of the drill block and insertable into an opening in the first surface of the bone plate in order to constrain rotational movement of the bone plate and the drill block with respect to each other when the first locking element is attached to the drill block and the bone plate Example 7 includes the bone plating system of example 6, wherein an angular orientation of the first locking element with respect to the drill block and an angular orientation of the second locking element with respect to the drill block are different.

Example 8 includes the bone plating system of example 6, wherein the angular orientation of the first locking element with respect to the drill block and the angular orientation of the second locking element with respect to the drill block are not parallel.

Example 9 includes the bone plating system of any one of examples 6-8, wherein the second locking element comprises a pin.

Example 10 includes the bone plating system of any one of examples 6-9, wherein the first locking element comprises a drill guide.

Example 11 includes the bone plating system of any one of examples 6-10, wherein the first locking element comprises a bore, a proximal end and a distal end, and the distal end includes threads for removable attachment to, or threadable engagement with, a threaded surface of the at least one drill block hole of the drill block and the one of the at least two bone screw receiving holes of the bone plate.

Example 12 includes the bone plating system of any one of examples 6-11, wherein the first locking element comprises a bore, a proximal end and a distal end, and the distal end includes threads for removable attachment to, or threadable engagement with the one of the at least two bone screw receiving holes of the bone plate Example 13 includes the bone plating system of any one of example 6-12, wherein the bore on the proximal end of the first locking element includes a plurality of indentations spaced apart on a periphery of bore for receiving a tip of a drill.

Example 14 includes the bone plating system of any one of claims 6-13, wherein the at least one drill block hole is configured to allow a bone screw to extend therethrough to the bone plate.

Example 15 includes the bone plating system of any one of examples 6-14, wherein the opening in the first surface of the bone plate is one of the at least two bone screw receiving holes.

Example 16 includes a method of fixating a fracture of a bone, comprising providing or obtaining a bone plate including a plurality of bone screw receiving hole; providing a drill block to be removably attached to the bone plate and including a plurality of drill block holes and a first locking element extending from the drill block; applying the drill block to the bone plate such that the first locking element is inserted in an opening in the bone plate; attaching the bone plate to the drill block by inserting a second locking element through one of the drill block holes and into one of the bone screw receiving holes that is aligned with the one of the drill block holes in order to constrain rotational movement of the bone plate and the drill block with respect to each other when the second locking element is attached to the drill block and the bone plate; applying the bone plate to the bone adjacent the fracture; drilling at least one hole into the bone by inserting a drill through a selected one of the drill block holes and an aligned bone screw receiving hole of the bone plate; and securing the bone plate to the bone by inserting a plurality of bone screws through the plurality drill block holes and the plurality of bone screw receiving holes, and into the holes drilled in the bone.

Example 17 includes the method of example 16, wherein attaching the bone plate to the drill block further comprises contacting a first surface of a bone plate with a first surface of the drill block, and wherein applying the bone plate to the bone further comprises contacting a second surface of the bone plate opposite the first surface to the bone adjacent the fracture.

Example 18 includes the method of any one of examples 16-17, wherein an angular orientation of the first locking element with respect to the drill block and an angular orientation of the second locking element with respect to the drill block are different.

Example 19 includes the method of any one of examples 16-17, wherein an angular orientation of the first locking element with respect to the drill block and an angular orientation of the second locking element with respect to the drill block are not parallel.

Example 20 includes the method of any one of examples 16-19, further comprising the steps of: removing the second locking element; and removing the drill block from the bone plate.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

What is claimed is:

1. A bone plating system comprising:
   a bone plate;
   a drill block removably attachable to the bone plate;
   a first locking element configured to be removably attached to the drill block and the bone plate by extending through an unthreaded drill block hole of the drill block and into an aligned receiving hole of the bone plate, the unthreaded drill block hole extending along a first axis, the first locking element including an externally threaded surface configured to engage an internally threaded surface of the aligned receiving hole; and
   a second locking element formed integral with the drill block and configured to extend along a second axis from the drill block and into an indentation in a side surface of the bone plate in order to constrain movement of the bone plate and the drill block with respect to each other when the first locking element is attached to the drill block and the bone plate;
   wherein the first and second axes are not parallel, thereby preventing removal of the drill block from the bone plate unless the first locking element is removed from the aligned receiving hole of the bone plate; and
   wherein the second locking element includes at least two flat surfaces, and wherein the indentation includes at least two complementary flat surfaces configured to engage the at least two flat surfaces of the second locking element to constrain movement of the drill block relative to the bone plate.

2. The bone plating system of claim 1, wherein the second locking element comprises a pin.

3. The bone plating system of claim 1, wherein the first locking element comprises a drill guide.

4. A bone plating system comprising:
   a drill block extending from a proximal end to a distal end and having a first surface for contacting a bone plate, a second surface opposite the first surface, an extended nose portion at the proximal end, and at least one unthreaded drill block hole extending from the first surface to the second surface of the drill block;
   a bone plate extending from a proximal end to a distal end and having a first surface for contacting the drill block, a second surface for contacting a bone, and at least two receiving holes extending from the first surface to the second surface of the bone plate, wherein one of the at least two receiving holes is alignable with the at least one unthreaded drill block hole, and wherein the extended nose portion of the drill block overhangs a periphery of the proximal end of the bone plate when the drill block is attached to the bone plate;
   a first threaded locking element configured to be removably attached to the drill block and the bone plate by extending through the at least one unthreaded drill block hole of the drill block and into the one of the at least two receiving holes of the bone plate that is alignable with the at least one unthreaded drill block hole; and a second unthreaded locking element extending from and formed integral with the first surface of the drill block and insertable into an indentation in a side surface of the bone plate in order to constrain movement of the bone plate and the drill block with respect to each other when the first locking element is attached to the drill block and the bone plate;

wherein an angular orientation of the at least one unthreaded drill block hole and an angular orientation of the second unthreaded locking element are different, thereby preventing removal of the drill block from the bone plate unless the first threaded locking element is removed from the one of the at least two receiving holes of the bone plate; and wherein the second locking element includes at least one flat surface, and wherein the indentation includes at least one complementary flat surface configured to engage the at least one flat surface of the second locking element to constrain movement of the drill block relative to the bone plate.

5. The bone plating system of claim 4, wherein the second locking element comprises a pin.

6. The bone plating system of claim 4, wherein the first locking element comprises a drill guide.

7. The bone plating system of claim 4, wherein the first locking element comprises a bore.

8. The bone plating system of claim 4, wherein the first locking element comprises a bore, a proximal end and a distal end, and the distal end includes threads for removable attachment to, or threadable engagement with the one of the at least two receiving holes of the bone plate.

9. The bone plating system of claim 8, wherein the bore on the proximal end of the first locking element includes a plurality of indentations spaced apart on a periphery of the bore for receiving a tip of a drill.

10. The bone plating system of claim 4, wherein the at least one unthreaded drill block hole is configured to allow a bone screw to extend therethrough to the bone plate.

11. The bone plating system of claim 4, wherein the bone plate comprises a humeral plate.

12. A bone plating system comprising:

a bone plate including a proximal end, a distal end, an upper surface, and a lower bone-contacting surface configured for placement on a humerus;

a drill block removably attachable to the bone plate, the drill block including a proximal end, a distal end, and an extended nose portion at the proximal end that extends proximally beyond a periphery of the proximal end of the bone plate when the drill block is attached to the bone plate, the extended nose portion including a lower bone-contacting surface configured to contact a proximal end of the humerus such that the extended nose portion projects tangentially with an articular surface of the humerus;

a first locking element configured to be removably attached to the drill block and the bone plate by extending through an unthreaded drill block hole of the drill block and into an aligned receiving hole of the bone plate, the first locking element including an externally threaded surface configured to engage an internally threaded surface of the aligned receiving hole, and a second locking element formed integral with the drill block and configured to extend from the drill block and contact a portion of the bone plate in order to constrain movement of the bone plate and the drill block with respect to each other when the first locking element is attached to the drill block and the bone plate;

wherein an angular orientation of the first locking element with respect to the drill block and an angular orientation of the second locking element with respect to the drill block are different, thereby preventing removal of the drill block from the bone plate unless the first locking element is removed from the aligned receiving hole of the bone plate.

* * * * *